United States Patent [19]

Pennig

[11] Patent Number: 5,356,410
[45] Date of Patent: Oct. 18, 1994

[54] ADJUVANT FOR OSTEOSYNTHESIS IN THE CASE OF PERTROCHANTERIC FRACTURE OF THE NECK OF THE FEMUR

[76] Inventor: Dietmar Pennig, Hans-Driesch-Strasse 12, 5000 Köln, Fed. Rep. of Germany

[21] Appl. No.: 75,495

[22] Filed: Jun. 8, 1993

[30] Foreign Application Priority Data

Dec. 13, 1991 [DE] Fed. Rep. of Germany ....... 4141152
Dec. 4, 1992 [EP] European Pat. Off. ........ 92120696.7

[51] Int. Cl.⁵ ............................................. A61B 17/58
[52] U.S. Cl. ........................................ 606/62; 606/69
[58] Field of Search ................. 606/60, 62, 64, 67, 606/69, 72

[56] References Cited

U.S. PATENT DOCUMENTS

| | | | |
|---|---|---|---|
| 3,716,050 | 2/1973 | Johnston | 606/69 |
| 4,733,654 | 3/1988 | Marino | |
| 5,108,449 | 4/1992 | Gray | 606/69 |
| 5,197,966 | 3/1993 | Sommerkamp | 606/69 |

FOREIGN PATENT DOCUMENTS

| | | |
|---|---|---|
| 0251583 | 6/1988 | European Pat. Off. |
| 0347874 | 12/1989 | European Pat. Off. |
| 3114136 | 10/1982 | Fed. Rep. of Germany ........ 606/69 |
| WO9109571 | 2/1991 | PCT Int'l Appl. |

*Primary Examiner*—Tamara L. Graysay
*Attorney, Agent, or Firm*—Hopgood, Calimafde, Kalil & Judlowe

[57] ABSTRACT

An adjuvant for osteosynthesis comprises an osteosynthesis plate which is capable of rigid connection to the axial end of a medullary nail. In the case of a pertrochanteric fracture of the femur, with a medullary nail in the proximal region of the femur, an external-end connection is provided for the osteosynthesis plate; and the osteosynthesis plate is provided with a distributed pattern of bores to accommodate bone screws, wherein bone screws of one kind are used for the fixation of the osteosynthesis plate to the femur, and bone screws of another kind are used for the fixation of the osteosynthesis plate to the neck of the femur. The bores are in transversely spaced array, at spacings that are greater than the diameter of the medullary nail, so that bone screws of each pair can bypass the medullary nail, on opposite sides of the medullary nail. In another embodiment, an osteosynthesis plate is fixed by bone screws to the head of a humerus, and the plate holes for the screws are on opposite sides of the axial projection of the upper end of a medullary nail in the humerus; a rigid axial-end connection of the medullary nail to the plate stabilizes the thus-connected end of the medullary nail and all bone-screw anchorages.

15 Claims, 2 Drawing Sheets

ADJUVANT FOR OSTEOSYNTHESIS IN THE CASE OF PERTROCHANTERIC FRACTURE OF THE NECK OF THE FEMUR

BACKGROUND OF THE INVENTION

The present invention relates to an adjuvant for osteosynthesis of a broken bone as in particular for the case of a pertrochanteric fracture of the neck of the femur, or a fracture of the upper arm.

U.S. Pat. No. 4,733,654 proposes the use of a special adjuvant for osteosynthesis in order to immobilize the neck and the head of the femur. Specifically, with this adjuvant, an additional nail part, namely, a separate medullary-nail part, is effectively an extension of the medullary nail and is capable of fixation in the proximal region of the medullary nail, and the nail-extension part features an inclined bore that is designed to accommodate an especially long bone-screw or pin. In that case, the osteosynthesis plate is L-shaped, comprising a side-plate, with a short, upper angularly oriented tubular leg or barrel formation which engages the inclined bore of the nail-extension part. As a consequence of the preset orientation of bores of the medullary nail, of the L-shaped side plate, and of the separate nail-extension part, the osteosynthesis adjuvant of this patent necessarily results in fixed directions of bone-screw or pin orientation, i.e., the attachment and orientation of bone-screws or pins cannot be varied.

BRIEF STATEMENT OF THE INVENTION

The object of the invention is to provide for better and more secure mechanical mounting of an osteosynthesis plate, by making the direction of bone screws or pins freely selectable, so that, with the simplest possible adjuvant, sufficient anchorage and immobilization of the femoral neck may be achieved, and so that the great trochanter can be immobilized by the osteosynthesis plate.

The invention achieves this object by providing an osteosynthesis plate with an integral, radially inward formation at its upper end, for directly secured connection to the upper end of an installed medullary nail, and by providing in the body off the plate a distributed plurality of bores that are adapted for accommodation of a plurality of bone screws or pins, over a range of screw or pin orientation at each of the bores.

In other words, it is proposed, for the case of a pertrochanteric fracture of the neck of the femur, to insert a medullary nail in the proximal region of the femur; the medullary nail reaches all the way to the great trochanter and features at its upper end a connecting device—for example, in the form of a bolt threaded to the proximal end of the medullary nail—for rigid connection to an osteosynthesis plate. The osteosynthesis plate features a plurality of holes for the accommodation of bone screws, the transverse spacing of the holes being greater than the diameter of the medullary nail, so that the direction of bone-screw orientation is not predetermined by corresponding accommodating bores in the medullary nail. As a consequence, bone screws through the holes in the plate may bypass the medullary nail on both sides and lead to the head of the femur, in that the direction of bone-screw advance is freely selectable.

In this manner, one may achieve a secure fixation of the neck of the femur and of the head of the femur to the proximal region of the femur, and this secure fixation is achievable essentially with the use of conventional instruments.

It is also proposed, in accordance with the invention, that in the further case of an upper-arm fracture in the region of the head of the humerus, there be provided an osteosynthesis plate that is capable of rigid connection to a medullary nail inserted in the humerus, in which case once again the osteosynthesis plate is equipped with holes designed to accommodate bone screws, and these holes are so arranged that the bone screws can bypass the medullary nail.

For some applications, it is desirable that the material of the osteosynthesis plate be deformable, to enable adaptation to the local contouring of an involved bone.

DETAILED DESCRIPTION

Illustrative examples of the invention will be described in conjunction with the accompanying drawings, in which.

Figures 1, 2:
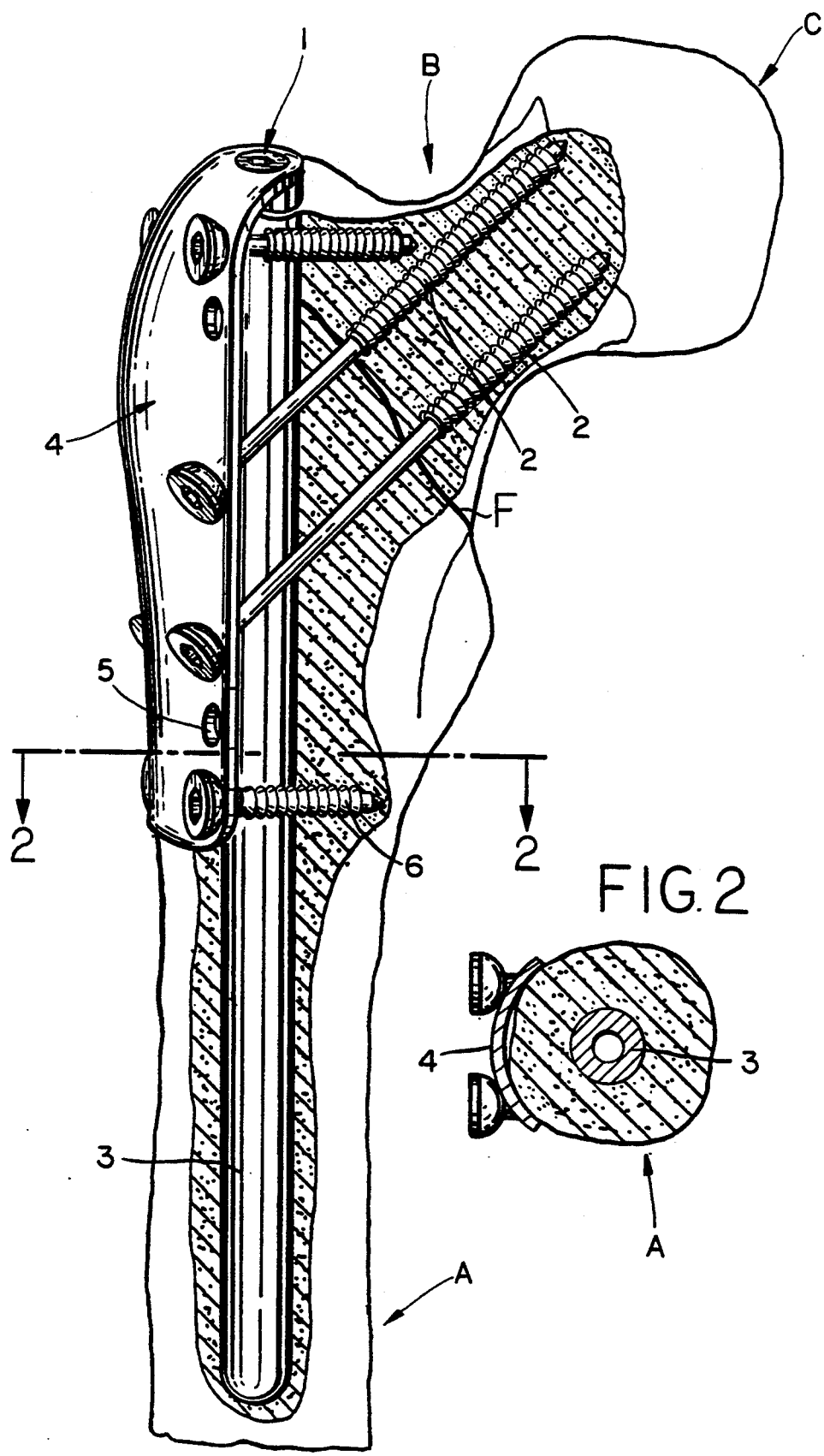
FIG. 1 is a perspective view of an adjuvant device of the invention, in application to the proximal end of a femur having a pertrochanteric fracture F, the view being partly broken-away and in section substantially in the plane determined by the respective longitudinal axes of the femur and of the femoral neck.
FIG. 2 is a section along the line 2—2 in FIG. 1.

In FIG. 1, A designates a femur, B the neck of the femur, and C the head of the femur. A medullary nail 3 is inserted in the proximal end of femur A, and the medullary nail features at its upper external end a threaded connection means 1, which enables rigid connection of an osteosynthesis plate 4 to the external end of medullary nail 3. The osteosynthesis plate 4 is shown downwardly extending beyond axial lap of the lesser trochanter, and plate 4 features a plurality of holes 5, through which long bone-screws 2 and short bone-screws 6 can be inserted. In so doing, the short bone-screws 6 fix the osteosynthesis plate 4 to femur A, while the long bone-screws 2 lead all the way into the head of the femur C, and thus fix this region to the femur; as shown, the underside of the heads of screws 2 and 6 are convex spherical for accurately seated engagement to plate 4, whatever their orientation. As shown clearly in FIG. 1, and also clearly in FIG. 2, the holes 5 for accommodating screws 2 and 6 are so transversely spaced that the inserted screws can run past both sides of the inserted medullary nail 3, and, in this fashion, lead to the head of the femur. As a consequence, no direct connection with the medullary nail is required, other than the axially threaded end connection at 1, thus obviating the need for expensive designs of the nail.

More particularly, as shown in FIGS. 1 and 2, the osteosynthesis plate 4 is generally cylindrically arcuate, about the shaft axis of the femur and therefore about the medullary nail, and plate 4 extends longitudinally in overlap with the medullary nail and in overlap with the lesser trochanter and the rest of the proximal end of the shaft of the femur. Plate 4 has symmetry about a longitudinal plane through the shaft axis, and the inward bend at the proximal end of the shaft is sufficient to lap the adjacent end of the medullary nail, being formed for acceptance of the threaded means (1) of fixation top the medullary nail. The mounting holes 5 in plate 4 are seen to be in pairs, at opposite lateral offset from the central plane of symmetry of the plate, the offsets being to provide such spacing between paired holes as to slightly exceed the diameter of the medullary nail 3. The pairs of holes 5 are longitudinally distributed along plate 4, to enable a pair of the short screws 6 top anchor into shaft bone, independently of the medullary nail and on opposite sides thereof, near the respective longitudinal ends of the plate; the distributed pairs of holes 5 preferably include two spaced pairs between the end pairs, for accommodation of the long screws 2 on acutely inclined orientations which enable appropriately inclined entry and extensive penetration into femoral-neck bone structure beyond the fracture F and via paths on opposite sides of the medullary nail. The central plane of symmetry of the plate 4, when thus installed, will be seen to substantially accord with the general plane defined by the respective axes of the shaft (A) and of the neck (B) of the femur.

Figure 3:
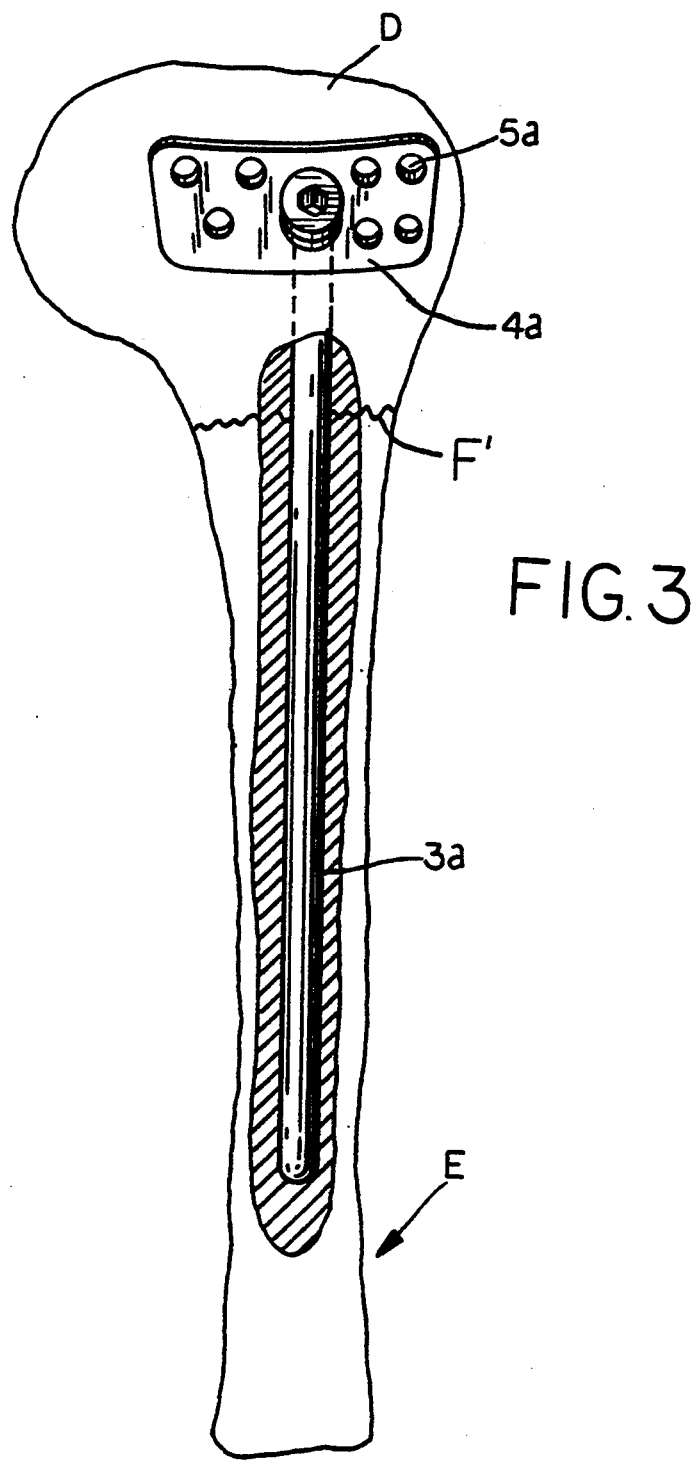
FIG. 3 is a view in elevation of the proximal end of a humerus fractured at $F^1$ and in association with another adjuvant device of the invention.

FIG. 3 shows another embodiment of the invention, in application to the head D of the humerus E, in which a medullary nail 3a has been installed. An osteosynthesis plate 4a will be understood to be fixed to the head D of the humerus, via mounting holes 5a for accommodation of fixation screws (not shown). The upper end of medullary nail 3a can be rigidly connected to this osteosynthesis plate 4a, via an externally actuable threaded axial connector (as shown). The position of the medullary nail is locked in place by the osteosynthesis plate when fixed to the head of the humerus.

What is claimed is:

1. An osteosynthesis adjuvant for use in a case of bone fracture, comprising a medullary nail and an osteosynthesis plate, said medullary nail having at an end thereof means for rigid connection to said osteosynthesis plate, said osteosynthesis plate having plural spaced bores designed to accommodate bone screws, and said bores being arrayed as longitudinally spaced pairs of transversely spaced holes, wherein the transverse spacing of paired holes is greater than the diameter of the medullary nail.

2. An adjuvant according to claim 1, wherein the osteosynthesis plate is capable of being deformed for adaptation to the contour of a given bone.

3. An osteosynthesis adjuvant for use in a case of bone fracture, comprising a medullary nail and an osteosynthesis plate, said medullary nail having at an end thereof means for rigid connection to said osteosynthesis plate, said osteosynthesis plate having plural spaced bores designed to accommodate bone screws, and said bores being in longitudinally spaced array along transversely spaced alignments, wherein the transverse spacing is greater than the diameter of the medullary nail.

4. The osteosynthesis adjuvant of claim 3, in which the medullary nail is of greater length than said plate.

5. The osteosynthesis adjuvant of claim 4, in which said plate is of generally cylindrically arcuate configuration that is symmetrical about a longitudinal plane through the axis of said generally cylindrical arcuate configuration.

6. The osteosynthesis adjuvant of claim 3, in which said plate is of generally cylindrically arcuate configuration and of greater arcuate extent than the diameter of the medullary nail, said plate having at its proximal end an integrally formed radially inward flange which is adapted for medullary-nail connection via said means for rigid connection, said plate having transversely spaced pairs of openings adapted to seat headed bone screws that are spaced for bone anchorage beyond bone-screw by-pass of the medullary nail on opposite sides of the medullary nail and substantially without restriction as to the angle at which given bone screws have headed seating at said openings.

7. The osteosynthesis adjuvant of claim 3, in which said osteosynthesis plate is elongate and transversely arcuate, and in which a longitudinal end of said plate is bent to extend radially inward of a geometric projection of the transverse arc, and in which said inwardly bent end is the means of rigid connection of said plate to said medullary nail.

8. An osteosynthesis adjuvant for use in a case of bone fracture, comprising a medullary nail and an osteosynthesis plate, said osteosynthesis plate having at an end thereof means for rigid connection to said medullary nail, said osteosynthesis plate having plural spaced bores designed to accommodate bone screws, and said bores being arrayed as longitudinally spaced pairs of transversely spaced holes, wherein the transverse spacing of paired holes is greater than the diameter of the medullary nail.

9. An osteosynthesis adjuvant for use in the case of a pertrochanteric fracture of a femur, comprising a medullary nail for the proximal region of a femur and an osteosynthesis plate having bores for mounting short and long bone screws, said medullary nail being of sufficient length to lap a greater trochanter and including at an external end means for establishing a connection to the osteosynthesis plate , the bores in the osteosynthesis plate being so transversely spaced to accommodate said bone screws that said bone inserted therein bypass both sides of the medullary nail; whereby said short bone screws may be used for fixation of the osteosynthesis plate to a femur, and said long bone screws may be used to lead from the outer side of the osteosynthesis plate in traverse of the fracture and all the way into a femoral neck.

10. An osteosynthesis adjuvant for use in the case of a fracture of a humerus, comprising a medullary nail for the proximal end of a humerus and an osteosynthesis plate having plural spaced bores for mounting bone screws, said nail being of sufficient length to extend both sides of a fracture and including at an externally accessible proximal end connection means for attachment to the osteosynthesis plate, the bores of said plate being transversely spaced to an extent exceeding the diameter of the medullary nail and configured to determine bone-screw alignments which bypass the medullary nail on both sides of the medullary nail.

11. The method of operatively bracing a femur for osteosynthesis repair of a pertrochanteric fracture, which method comprises:

(a) selecting and installing an elongate medullary nail in the proximal end of the femur;

(b) selecting an elongate osteosynthesis plate having longitudinally spaced pairs of bores that are transversely spaced to an extent exceeding the diameter of the medullary nail;

(c) securing the plate to the proximal end of the medullary nail with the plate extending longitudinally along the side of the femur that is opposite the side from which the femoral neck extends;

(d) aligning and setting at least one pair of relatively long bone screws via one pair of bores and on opposite sides of the medullary nail and aligned for anchorage within the femoral neck after bone-screw traverse of the fracture; and (e) aligning and setting at least one further pair of relatively short bone screws via another pair of bores and on alignments on opposite sides of the medullary nail and for anchorage in the femur at longitudinal offset from the anchorage of the relatively long bone screws of step (d).

12. The method of claim 11, in which the length of said plate is selected to extend distally at least to axial overlap with the lesser trochanter.

13. The method of claim 11, in which the length of the medullary nail is selected to extend distally beyond axial overlap with said plate.

14. The method of claim 11, in which said plate is selected for generally cylindrically arcuate conformance with the shaft of the femur and is applied to the side of the shaft which is opposite juncture of the femoral neck to the shaft.

15. The method of claim 14, in which said plate is selected for symmetry about a longitudinal plane defined by the axis of generally cylindrical curvature, and in which said plate is applied to the femur such that said longitudinal plane substantially conforms to the geometric plane defined by the axis of the femoral neck and the axis of the shaft.

* * * * *